United States Patent
Henderson et al.

(10) Patent No.: US 9,582,838 B1
(45) Date of Patent: Feb. 28, 2017

(54) TARGETED SURVEILLANCE SYSTEM WITH MINI-SCREEN DASHBOARD

(71) Applicant: Health Care Systems, Inc., Montgomery, AL (US)

(72) Inventors: William Dwight Henderson, Pike Road, AL (US); Reubin B. Felkey, Pike Road, AL (US)

(73) Assignee: Health Care Systems, Inc., Montgomery, AL (US)

( * ) Notice: Subject to any disclaimer, the term of this patent is extended or adjusted under 35 U.S.C. 154(b) by 280 days.

(21) Appl. No.: 14/194,711

(22) Filed: Mar. 1, 2014

Related U.S. Application Data

(60) Provisional application No. 61/771,160, filed on Mar. 1, 2013.

(51) Int. Cl.
 *G06Q 50/22* (2012.01)
 *G06F 19/00* (2011.01)

(52) U.S. Cl.
 CPC ......... *G06Q 50/22* (2013.01); *G06F 19/3406* (2013.01); *G06F 19/322* (2013.01)

(58) Field of Classification Search
 CPC ...... G06Q 50/22–50/24; G06F 19/322–19/327
 USPC ....................................................... 705/2–3
 See application file for complete search history.

(56) References Cited

U.S. PATENT DOCUMENTS

| | | | |
|---|---|---|---|
| 5,805,163 A | 9/1998 | Bagnas | |
| 7,046,254 B2 | 5/2006 | Brown | |
| 7,275,089 B1 | 9/2007 | Marshall | |
| 7,774,215 B2 | 8/2010 | Rosow | |
| 8,489,735 B2 | 7/2013 | Befort | |
| 8,510,126 B2 | 8/2013 | Martin | |
| 2004/0249676 A1* | 12/2004 | Marshall | G06F 19/327 705/2 |
| 2008/0154642 A1 | 6/2008 | Marble | |
| 2009/0024414 A1 | 1/2009 | Mansour | |
| 2010/0114599 A1* | 5/2010 | Lanning | G06Q 50/22 705/2 |
| 2011/0077968 A1* | 3/2011 | Kelly | G06F 19/345 705/3 |
| 2012/0095778 A1 | 4/2012 | Gross | |

(Continued)

*Primary Examiner* — Sheetal R Paulson
(74) *Attorney, Agent, or Firm* — CreatiVenture Law, LLC; Dennis J M Donahue, III

(57) ABSTRACT

A method and system for a mini-screen dashboard is described with reference to healthcare workflow processes where multiple healthcare providers work together to manage their patients. The status criteria for patients is collected in one or more healthcare workflow databases accessible by the clinicians according to their various roles and functions using corresponding workflow applications. A central computer determines the number of patients that correspond with various status criteria of the patients that are already being monitored by the clinicians and the mini-screen unobtrusively displays the number patients that meet the status criteria in a series of indicator boxes that remain in the foreground of the clinicians' respective computer screens. The mini-screen dashboard is semi-transparent, becoming opaque when a box is selected and displaying the heading name of the status criteria corresponding with the selected box and also displaying the names of the patients satisfying the status criteria.

14 Claims, 5 Drawing Sheets

(56) References Cited

U.S. PATENT DOCUMENTS

2012/0130730 A1* 5/2012 Setlur .................... G06Q 50/22
705/2

* cited by examiner

TARGETED SURVEILLANCE SYSTEM WITH MINI-SCREEN DASHBOARD

CROSS-REFERENCE TO RELATED APPLICATIONS

This application claims priority from U.S. Provisional Patent Application Ser. No. 61/771,160 filed on Mar. 1, 2013 which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to automated monitoring and reporting systems, and more particularly to a monitoring and reporting system that includes a targeted surveillance system with a mini-screen dashboard.

Related Art

Healthcare monitoring and reporting systems use dashboards to monitor patient populations and workflow processes of the healthcare staff for circumstances where intervention is necessary. These dashboards are typically built on databases employing open source interface standards to aggregate structured and unstructured data from multiple points of entry. They then poll that database on a scheduled time period looking for specific criteria that may be of interest to the clinicians utilizing the dashboard. Examples of various patient monitoring and clinical workflow systems are described in U.S. Pat. Nos. 7,774,215 and 8,510,126 and in US Pat. Pub. No. 2012/0095778 which are incorporated by reference.

These dashboards generally display on a large screen monitor in a central location. They are typically made to take over the entire screen and force that screen to serve a single purpose in displaying the desired information about the relevant patient population. Because they are in a central location and visible to a large number of personnel, they are forced into only displaying information that is relevant to the entire population of medical personnel for whom the dashboard will be visible.

For this reason, these dashboards are generally built to address a few global issues (rooms that are ready to be cleaned or have patients to be placed there; patients that have medications that are due to be administered; patients that have pushed the call button and require nurse attention etc). Traditional dashboards are also only visible when the personnel seeking information are in the central location and looking at the screen on which the dashboard is displayed or when the user specifically requests a view of the dashboard. Because the dashboards are designed to be the only thing easily viewable on the screen, it does not enable the push of information while clinicians are engaged in other activities and the workflow application is not running. These details limit the utility of the dashboard to be able to focus on the specific needs of individual staff members while at the same time limiting access to the information available in the dashboard.

Also, recognizing that monitoring multiple patients may make it more challenging for healthcare providers to read the physiological parameters for all of the patients, the Gross '778 Published Application describes a system that expands and collapses display sectors depending on the information being provided. However, the expanding and collapsing of display sectors is still based on the basic concept that the status indicators themselves for each one of the patients must be displayed rather than collecting the status indicators in a way that can minimize the display to a fraction of the display required for monitoring the individual status indicators.

Outside of healthcare, applications that communicate information that may be of interest to a specific person have overcome the above issues by utilizing a much smaller section of the screen's available space to convey information. Typically, the application displaying this information is transparent to the point of being unobtrusive to the user experience unless the user moves the cursor over the application displaying the information. At this point it becomes opaque and the user can interact with the application to drill down for more detailed information. Another format of these applications is to place one or more active elements in the system tray or taskbar that is typically located along the edge of the desktop display (usually at the bottom, although some systems allow the taskbar to be relocated along the side or at the top of the desktop display). Examples of the above technology can be seen in weather gadgets which draw on databases to display current weather conditions, forecasts and other weather related items. Some of these weather gadgets may be displayed over any application that is open on the desktop while other weather gadgets may be displayed in the taskbar. Other examples of such gadgets are the system icons for a computer, such as the date/time information, printer status, power management, and other control panel items that periodically change. With some of these gadgets, alerts may be temporarily displayed and then disappear. Other alerts may stay displayed on the screen until the user clears the alert screen by selecting the close-display button.

Although these weather gadgets and computer gadgets are able to dynamically receive and graphically display information from a database system and may even permit the user to customize their own unique display and provide limited information to the system about their preferences, such as the user's location and types of alert messages the user wants to receive, these previously known gadgets are not used as a part of an overall workflow process which requires the coordination between multiple individuals having a variety of different roles and functions in the workflow process. Accordingly, these known gadgets have mostly a one-way flow of information from the system to the use and are not interactive with the user. Additionally, these known gadgets are not selecting surveillance information for the user based on their role and function in any workflow process that is shared with other users.

It is also known to have control rooms with one or more central dashboard displays or video walls and individual technicians have more specialized dashboards at their respective stations with information directed to their particular functions and roles within the overall organization. Examples of such control rooms are found in a number of industries in addition to healthcare, such as aviation and space, power generation, communications, broadcasting, manufacturing controls, policing, military, customer service, order processing and fulfillment, etc. These control room dashboards are based on the central location model with distributed specialty stations, and even the specialized dashboards at the technicians' stations are designed to be the primary display on the screen. In fact, in many systems where a technician may need to perform other work in addition to monitoring their dashboard screen, they either use a second screen or they are provided with a large display screen with a split screen so that the view of the dashboard is not impeded. Although these control room and dashboard systems certainly communicate information to the overall central control room as well as the technicians' stations, they do not enable the push of information to the individual technicians' stations to change an unobtrusive display of a particular selection of surveillance criteria based on the respective roles of the technicians where the unobtrusive display partially overlays other displays that are on the respective screens of the individual users. In the particular example of a technician with more than one screen so that a dashboard can have its own entire screen, even though all of the information is provided on the dashboard display, it would be beneficial to have certain critical dashboard information also shown on the non-dashboard screen as a foreground overlay or foreground taskbar. This could be particularly helpful if time-sensitive alerts are periodically displayed on the dashboard screen, especially if the technician has other duties that occasionally require their attention be directed to the other screen, such as composing an e-mail message regarding upcoming maintenance of one of the systems being monitored or working on a status report, or the technician may even have to leave their station for a period of time, such as to physically check on one of the systems.

SUMMARY OF INVENTION

Generally, the invention is a method and a system for a mini-screen dashboard that can be used with the larger known dashboard methods and systems. The mini-screen dashboard does not replace the monitoring of all status on larger dashboards, such as the physiological conditions and statuses of individual patients. Instead, it uses the same information that are used for the patients being monitored on these larger dashboards and collects the information together in a new and different way so that there can be a very small mini-screen dashboard that stays in the foreground of the computer screens that caregivers and other healthcare clinicians may use for a variety of tasks that may take them away from monitoring one of the larger standard dashboards. The mini-screen dashboard is particularly beneficial in situations where multiple healthcare providers work together to manage their patients.

The data for the mini-screen dashboard is based on status criteria for patients that are collected in one or more healthcare workflow databases which are accessible by the clinicians according to their various roles and functions using corresponding workflow applications. A central computer determines the number of patients that correspond with various status criteria of the patients that are already being monitored by the clinicians and the mini-screen unobtrusively displays the number patients that meet the status criteria in a series of indicator boxes that remain in the foreground of the clinicians' respective computer screens. The mini-screen dashboard is semi-transparent, becoming opaque when a box is selected and displaying the heading name of the status criteria corresponding with the selected box and also displaying the names of the patients satisfying the status criteria.

BRIEF DESCRIPTION OF THE DRAWINGS

The present invention will become more fully understood from the detailed description and the accompanying drawings. The drawings constitute a part of this specification and include exemplary embodiments of the invention, which may be embodied in various forms. It is to be understood that in some instances, various aspects of the invention may be shown exaggerated or enlarged to facilitate an understanding of the invention; therefore the drawings are not necessarily to scale. In addition, in the embodiments depicted herein, like reference numerals in the various drawings refer to identical or near identical structural elements.

DETAILED DESCRIPTION OF THE PREFERRED EMBODIMENTS

Figure 1:
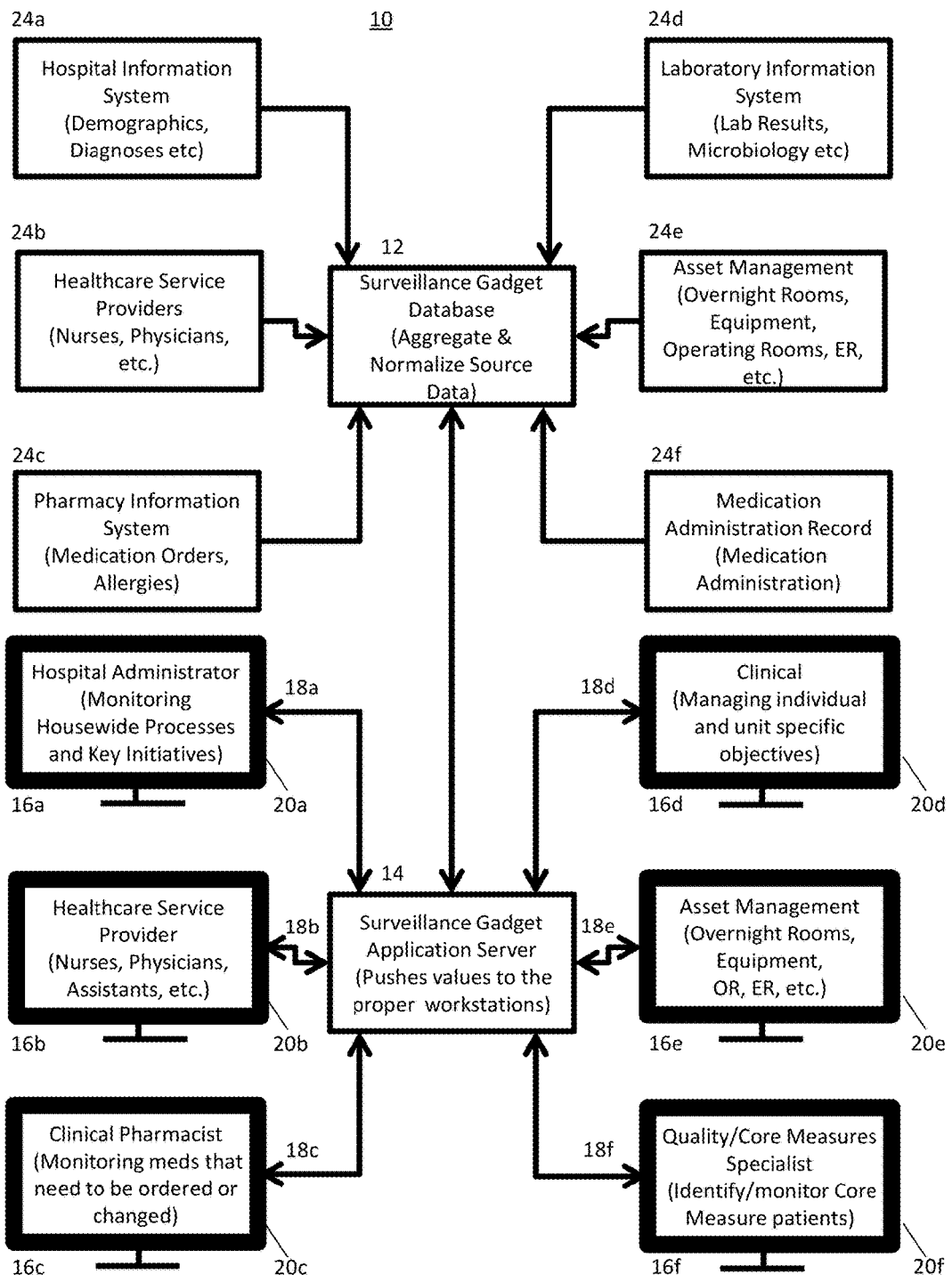
FIG. 1 is a system diagram of the data communications between the mini-screen dashboard application and other systems in the healthcare workflow processes.

The following description of the inventive Surveillance Gadget (SG) system 10 is merely exemplary in nature and is in no way intended to limit the invention, its application, or uses. The SG system 10 uses many of the same open source interface standards found in other healthcare focused dashboards as well as direct database queries and other methods of data aggregation to create a robust centralized database 12 on which analytics and surveillance can be performed using a computer processor 14 which is communicated to workflow computers 16 through a networked communication system 18. The system 10 uses the standard monitor screens 20 of the workflow computers with a unique mini-screen dashboard 22 that is configurable by system managers or the individual users to display the specific criteria 34 most useful to their tasks and area of expertise. The SG system evaluates the status information from multiple patients and groups them together so that the mini-screen dashboard 22 is a fraction of the size required by standard dashboard display, allowing the mini-screen dashboard to always be shown on the foreground of the monitor screen without being obtrusive. This foreground display causes the mini-screen dashboard to remain visible on the screen or screens where the system users perform the majority of their job requirements. The aggregation of data by the system from multiple sources 24 of information and the configuration variations based on the roles and functions of various individuals 16a-16f are generally shown in FIG. 1. It will be appreciated that the system 10 may use the aggregation from multiple workflow systems 24 that is performed for the standard central system dashboards which do not combine the status information as is done by the computer 14 in the present invention.

Figure 2:
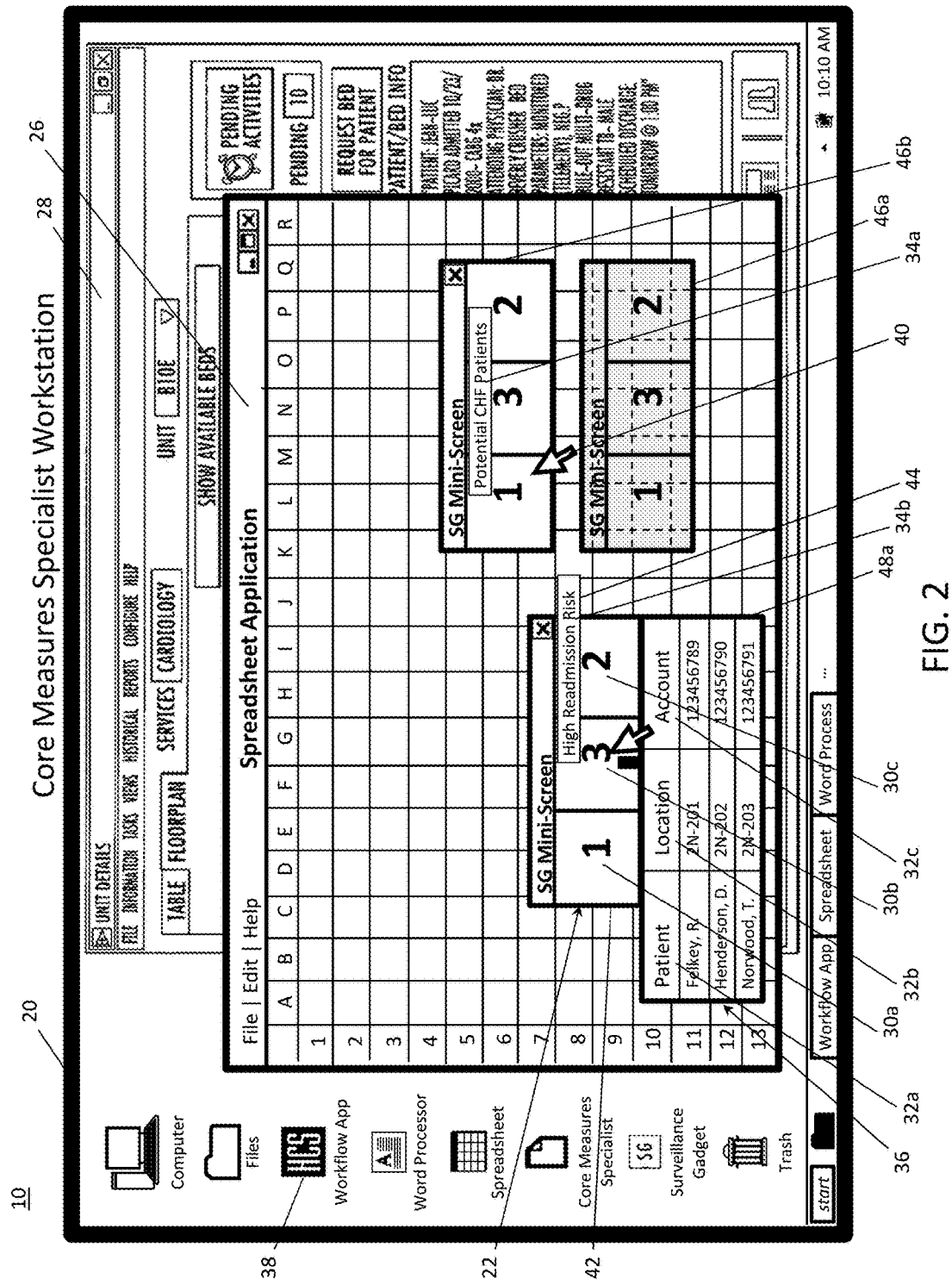
FIG. 2 shows a monitor screen displaying the mini-screen dashboard according to the present invention.
Figure 3:
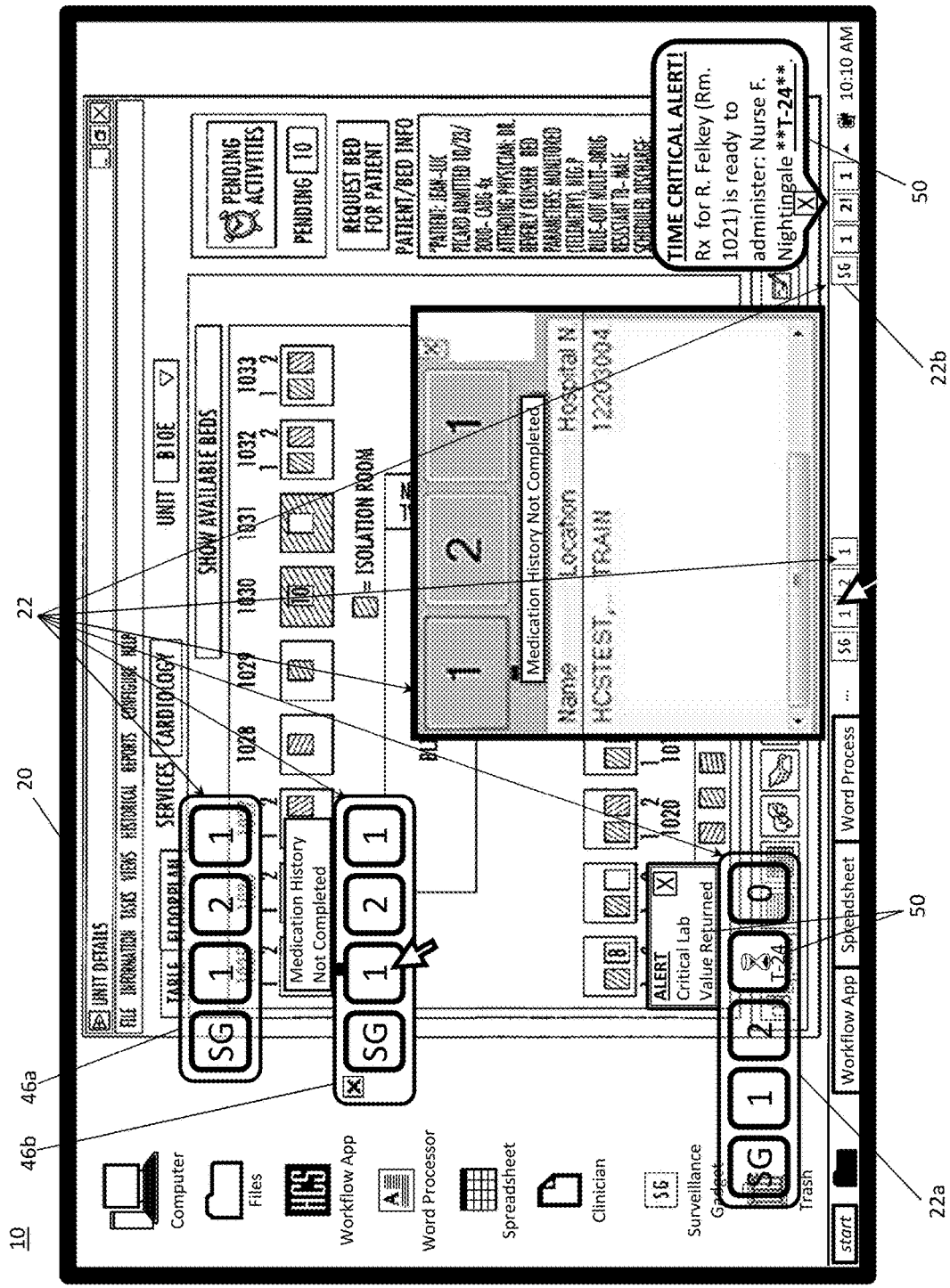
FIG. 3 shows alternative locations, configurations and arrangements of the mini-screen dashboard according to the present invention.

Users can interact with the mini-screen dashboard of the SG system 10 to drill down to specific information 36 or open the relevant application 38 in a context sensitive manner to address the identified issue. An example of the system's mini-screen is shown in FIG. 2 as it may appear on a workstation that is running a spreadsheet application 26 and a workflow application 28, such as a core measurement specialist 16f may do during normal activities. Generally, the numbers 30 within the mini-screen indicator boxes 42 correspond with the number of patients 32a that meet a particular criteria 34. For example, as particularly shown in FIG. 2, there is one (1) patient that meets the criteria of having a potential for congestive heart failure (i.e., "Potential CHF Patients") 34a. Another criteria may be patients with high risk for readmission 34b which could be the three (3) patients listed in the middle box. The other box may be an indication of patients on a unit who have new lab orders or prescriptions ready at the pharmacy, i.e., two (2) patients. Alternative locations of the dashboard mini-screen are shown in FIG. 2 and FIG. 3.

The system's computer 14 monitors criteria in the database 12, calculates the number of patients that meet the criteria items that are being tracked on the dashboard mini-screens 22 and periodically increments or decrements the numbers based on the updates to the database. When the cursor 40 is placed on or hovers over a number in the mini-screen, the system preferably displays the heading name 44 of the criteria 34 that is indicated by the number 30. The number of indicator boxes 42 displayed in the mini-screen dashboard is a configurable selection. For example, most examples shown in the drawings have three (3) active boxes, and some have an application configuration launch button (SG) and one example in FIG. 3 shows four (4) active boxes as one alternative configuration.

The SG system 10 overcomes the limitations of existing health care focused dashboards by using a display technology that is similar to weather gadgets and system icons which display relevant information while taking up a much smaller portion of the screen, but the SG system 10 combines the status information for multiple patients being monitored so that the display technology can be delivered and used in a much different way than typical gadget applications. The information that is pushed to particular workstations is based primarily on the roles and functions of the user who is logged into the system 10 through the workstation computer 16. By collecting the information of various criteria being monitored and calculating the number corresponding to each of the categories, the grouped information can be displayed as the number of active workflow tasks for each monitored criteria. As discussed in detail below, different types of computers may be used with the SG system 10 according to their ability to serve the system users and their differing roles and functions.

It will be appreciated that any number of active boxes 42 can be selected for a mini-screen configuration 22a, 22b that meets the particular needs of the corresponding user. It will also be appreciated that although the number of patients 30 that meet particular criteria 34 is the indicator used in the present examples, other criteria for the indicators may also be used by the system. For example, when the system is used by a pharmacist, one of the numbers may identify the number of prescriptions that need to be filled while another number can represent the number of medicines that may be running low and should be checked for reordering. As indicated below, the indicators for some criteria 34 may be any type of textual, alphanumeric or even graphical display depending on what best conveys the information to the system user in the mini-screen dashboard format.

When the user selects the field box 30 in the mini-screen 22, the system displays additional information 32 from the database 12 about the particular criteria 34. In the patient examples provided above, the additional information about the patients in the database who meet the criteria could include the patient names 32a and their respective room numbers 32b and may include other information, such as an identification number 32c that is unique to each patient or other personally identifiable information (PII). The additional information is preferably displayed in a drop-down window 48a connected to the mini-screen 22 or can alternatively be displayed in its own pop-up window 48b. When the user selects one of the patient records, the system can automatically launch the appropriate application 38 so that the system user can perform any required review or intervention of that patient record. If the application is already running but is hidden behind another application display, the system can pull the application to the foreground although the mini-screen dashboard always remains visible either on the top of the foreground application or in the foreground taskbar.

The SG system pushes information directly to system users when and where they need it. This timely push of relevant data will allow system users to more easily determine when a specific action needs to occur (critical lab value that needs to be responded to, medication history needs to be gathered, patient has been diagnosed with a specific condition and needs certain medications started, etc.). Healthcare administrators will be able to monitor the speed with which clinical actions are taking place, identify trouble areas and assign additional resources as necessary. The Surveillance Gadget system can be specifically configured to display different information based on the computer on which it is installed or the user who is viewing it. This information is always viewable by the user of a particular workstation in the mini-screen dashboard as either a foreground overlay or in the foreground taskbars, and the mini-screen dashboard remains unobtrusive except when one of its displayed items is selected.

As indicated above, in FIG. 2, the mini-screen display is shown as a foreground overlay mini-screen on a monitor 20 that is displaying a spreadsheet application 26 that is over a display for a workflow application 28. The foreground overlay is an example of a mini-screen dashboard that is always open and displayed within the application portion of the clinical workstations' screens. The user can move the mini-screen to an unobtrusive position on the screen and to further reduce the impact of the blockage of the primary application, the mini-screen is preferably displayed in a partially transparent form 46a. As with the location of the mini-screen, the user may adjust the transparency of the mini-screen to reduce the intrusiveness of the overlay. The amount of transparency, and the location of the mini-screen may change depending on the applications that are being run. The size of the mini-screen can have an area that is less than approximately one twentieth the area of the entire display, even when the display is a tablet computer or a smart-phone screen, so it is not a significant challenge for the clinicians to place the mini-screen in an unobtrusive location. When the user places the cursor 40 anywhere on or hovers over the mini-screen, the system removes the transparency of the mini-screen and displays an opaque version mini-screen dashboard 46b. It will be appreciated that when the SG system 10 is being run on a computer with a touchscreen, such as on a tablet computer or a smart-phone, the user's finger combined with the touch-sensitive positioning elements in the screen can function as the cursor.

Examples of different types of arrangements for the mini-screen dashboard are shown in FIG. 3. One arrangement is the foreground overlay mini-screen 22a, and FIG. 3 also shows a foreground taskbar mini-screen 22b as another arrangement of the mini-screen dashboard 22. These examples of mini-screen arrangements are shown on a monitor 20 that is displaying a computer application for a hospital bed management system 28. As with the foreground overlay mini-screen dashboard, the foreground taskbar mini-screen is always open. However, rather than being displayed within the application portion of the clinical workstations' screens, the foreground taskbar mini-screen is displayed in the periphery of the desktop display, preferably along one of the edges of the screen.

The Surveillance Gadget system is particularly useful in time sensitive applications. When using typical dashboard systems, the system users often find themselves logging into applications to see if results have been returned. Many applications do not do a good job of alerting the users when new information has been received in a dashboard system, even when the information is time sensitive. With the present system, when time sensitive or other important information has been entered into the system, the mini-screen dashboard can provide an alert 50. Exemplary displays of such alerts are shown in FIG. 3 for both types of mini-screen dashboards. Some time-critical, important alerts for nurses or doctors could be that a critical lab value has been resulted or an important medication has been ordered and is ready to be administered. As another example of an important, time-critical alert may be a notice provided to clinical pharmacists that a patient has just come out of surgery. The pharmacists are responsible for ensuring that patients receive antibiotics immediately after surgical procedures, but they often struggle with identifying patients who meet the criteria to receive these antibiotics in a timely manner because the current systems do not have a good way of getting this information directly to the pharmacists in a timely manner.

As generally discussed above, alternative identifiers may be used to particularly note that there is an alert item that the user needs to review. For example, as shown in FIG. 3, an exclamation point (!) could be used in combination with the patient number. For time-critical alerts, a countdown clock may be displayed. The countdown clock could have an icon, such as an hourglass or a watch face along with an actual counter of the time remaining for the particular action to be performed. A shorthand notation can be used for the time remaining, such that the time to a deadline can be shown in shorthand as "T-time" which stands for "T minus time remaining" (i.e., T-24 is equivalent to 24 minutes remaining until the deadline time). The system can change of color or otherwise highlight the alert items and can also change the boxes to be opaque for the alert items. Additionally, when an alert first appears, the system can also add an alert mini-screen proximate to the mini-screen dashboard. Preferably the alert mini-screen is opaque and identifies the particular item in the mini-screen dashboard that is the subject of the alert. The alert mini-screen also preferably displays a brief description of the reason for the alert and may even identify the action that needs to be performed as well as the staff member that the system identifies as having primary responsibility to ensure that the action gets performed in a timely manner. The alert is preferably displayed on the screen until the user clears the alert screen.

The system user can clear the alert system by selecting the close-display button, but if the action is not taken within a particular time set by the system, the system will cause the alert to reappear and may take additional actions, such as adding an alert to a colleague who is also in communication with the Surveillance Gadget system and the supervisor of the responsible staff member. Depending on the particular function of an indicator box, a user can confirm or verify that the corresponding parameter has been reviewed for one of the patients corresponding with the displayed number or other item which causes the number in the box to be reduced by the patient for whom the task was completed. For example, for an indicator box that identifies patients where medication reconciliation has not been completed, the nurse would enter the information into the "med rec" system's database. As indicated below, it is possible that some databases within a hospital may not directly communicate with each other, and in this instance, the SG system may provide an efficient interface in collecting and aggregating the information from such segregated databases. Other examples include providing an alert for patients with a new lab order in which case, the SG system may determine whether something should be documented in one of the other patient management systems to demonstrate that the order has been reviewed. If the task is already documented in the other system, the SG system would receive some trigger indicating that the task is completed so that the caregivers are not having to repeatedly enter the same information multiple times in different systems.

As indicated above, the user can use the mini-screen dashboard, particularly including any alert, to launch the appropriate application 38 to perform any required review or intervention corresponding with the item. Since the Surveillance Gadget system is in communication with the other workflow systems, when the user responds to the alert by actually performing any necessary action and reporting the updated status in the appropriate application, the workflow system automatically communicates the status update to the Surveillance Gadget system which then automatically clears the alert.

In the example of a prescription order that has been received from the pharmacy, and the prescription medicine needs to be administered in a timely manner, the alert may identify the patient and their room as well as the primary care nurse who is responsible to administer the delivery of the medicine to the patient. Additionally, the alert can list the time remaining in which to administer the prescription medicine before a time-critical deadline or to otherwise perform the action within a timeframe that the management has defined as being a timely response. It is possible that multiple alerts could exist in a single mini-screen dashboard. For example, one alert could be a notice that a critical lab value has been returned while another alert could be a time-critical action, such as delivering an important prescription medicine that is very time sensitive for its desired efficacy.

Figure 4:
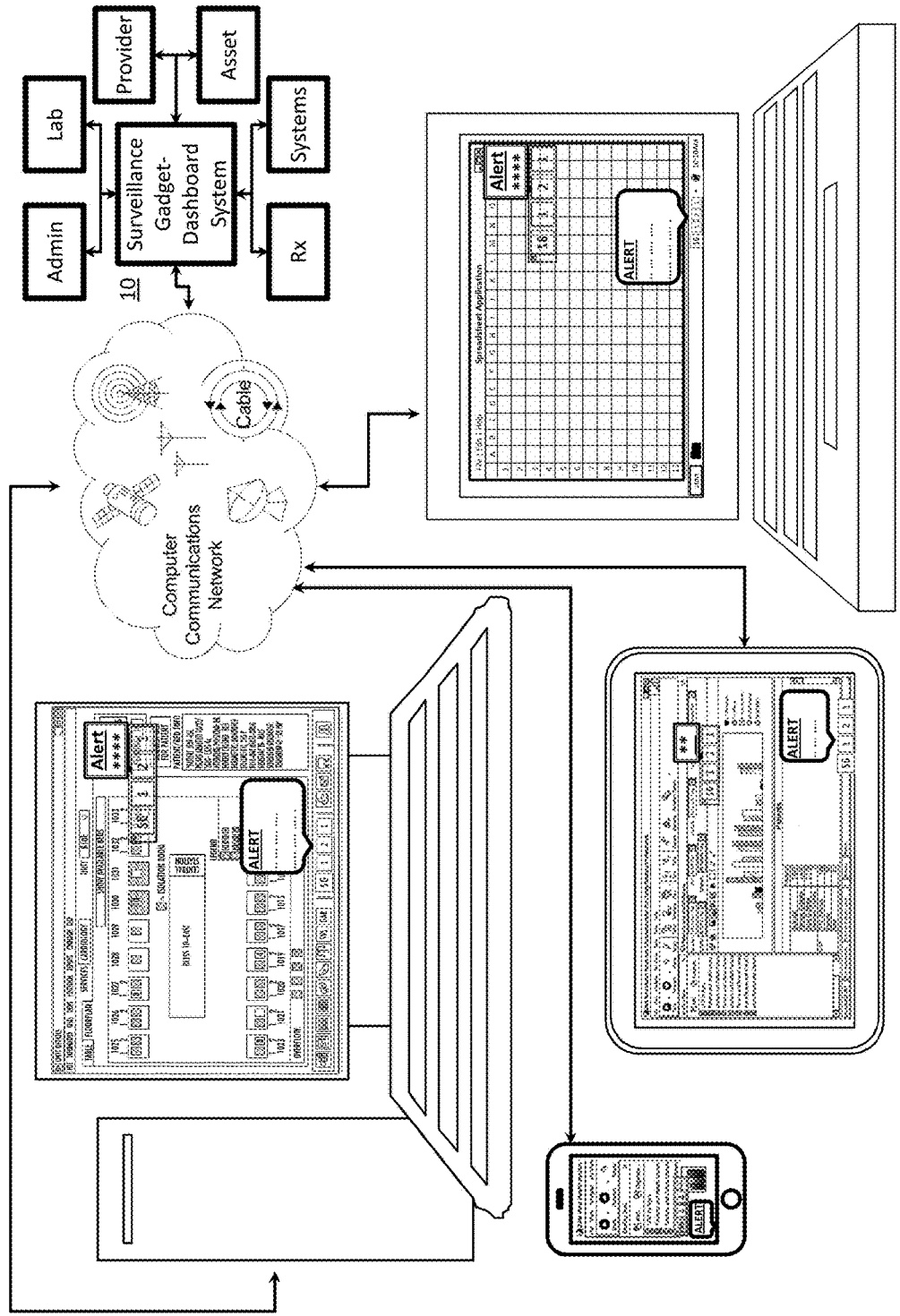
FIG. 4 shows the mini-screen dashboard displayed on different computer platforms.

Any computer platform can implement the mini-screen dashboard aspect of the Surveillance Gadget system, particularly including the updating of the mini-screen based on the Surveillance Gadget system's linkage to workflow systems and the alert feature. Several computer platforms are shown in FIG. 4, including a desktop computer, a laptop computer, a tablet computer and a smart-phone. The system can be configured to work with any type of computer platform and can be optimized for the particular usage by the various roles that are being performed in the various steps of the workflow processes. For example, a desktop computer would probably be preferable for nurses to use at a nursing station and the pharmacists in a hospital pharmacy, and a laptop computer could be used by nurses around the rooms in their ward, and physicians may like to use a tablet computer while making their rounds. The staff of a hospital equipment delivery service would likely be using a smart-phone, a tablet computer or some other lightweight mobile communications device while they make their deliveries and a central delivery coordinator would probably use a desktop computer. Accordingly, the computer tools may vary based on the work being performed. Of course, the particular applications that are being run by the various staff members would also depend on the work that they perform. The common aspect of their systems would be the use of the mini-screen dashboard according to the present invention in the foreground display, preferably including the collection and aggregation of information from one or more workflow databases, the calculation of the number of patients who meet the criteria for the fields represented in the indicator boxes, the activation of workflow applications that correspond with the particular indicator boxes, and the display of alerts with the mini-screen dashboard.

Figure 5:
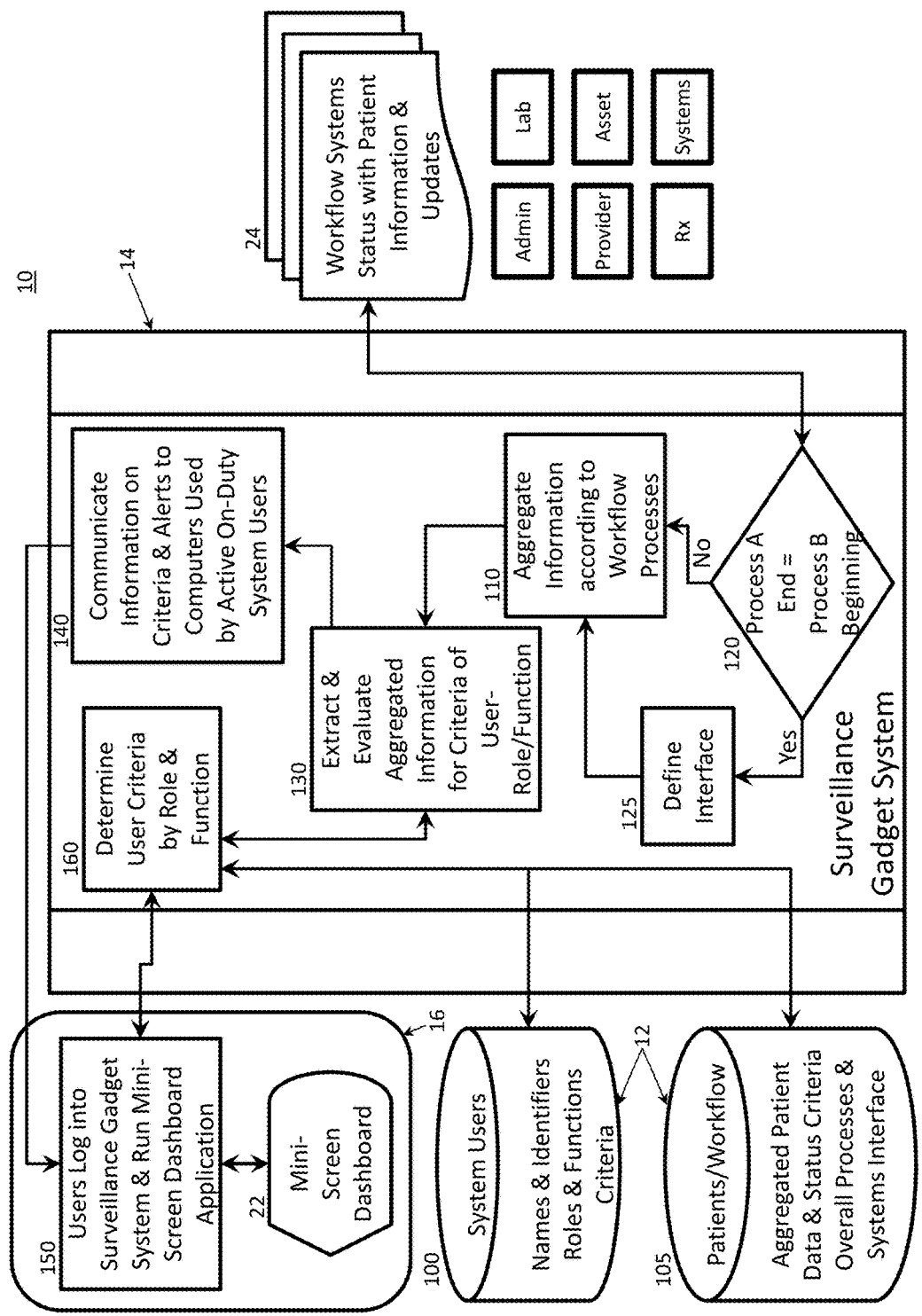
FIG. 5 is a flowchart of the mini-screen dashboard invention integrated into and interacting with multiple workflow systems.

The connection of the SG system 10 to multiple workflow systems can provide for improved efficiency throughout an organization. The relationship of the system 10 to multiple workflow systems 24 and the resulting benefits are generally shown in FIG. 5 as a process flowchart, and the time-critical medication is used as a particular example to explain this process in detail. An alert item or any other item listed in the mini-screen dashboard can be a part of an entire workflow process with multiple staff members who each has their own mini-screen dashboard 22. For a particular workflow process that has staff members who work on different workflow systems, the SG system 10 can be set up to link the workflow actions by the roles of the various staff members and their interrelationships in the sequence of the workflow actions (i.e., a new prescription for a patient in a hospital room cannot be administered by the nurse until the hospital pharmacy has dispensed the prescription medicine to the nursing station for a patient care unit and the hospital delivery service has delivered the medicine). Accordingly, the Surveillance Gadget system can serve as an interface between workflow systems which would not otherwise continue a process from one workflow system (i.e., pharmacy) to another workflow system (i.e., delivery & nursing) to provide continuity.

All of the users from each one of the workflow systems and their corresponding roles 100 are set up in the Surveillance Gadget system. The various workflow systems have these roles as a part of their workflow processes and contain at least a subset of the users depending on the scope of the workflow system. The Surveillance Gadget system aggregates the information from the various workflow systems 110, including the staff members that are listed as active on the current work shift of the respective workflow systems. The Surveillance Gadget system tracks the status of the workflow processes and continually makes updates as it receives updated information from the workflow systems, particularly the status of patients and ancillary medical equipment and service, services, supplies, and other items being monitored in the various systems 105.

When a workflow process extends over multiple workflow systems, the Surveillance Gadget system provides an interface between the workflow systems by providing a link between the end of a process in one workflow system and the beginning of a workflow process in another workflow system 120. For example, the time-critical prescription medicine discussed above may be required to be dosed more frequently than every four (4) hours or may be a need for rapid-acting insulin or it may be some other medication that is defined by the hospital as time-critical (i.e., limited number of medications for which early or delayed administration of more than 30 minutes before or after a scheduled dosing time might harm the patient, reduce the therapeutic effect of the treatment, or otherwise negatively affect the patient's treatment. Upon filling the prescription, the pharmacist could have entered the status update into the pharmacy workflow system. The pharmacy may have its own internal delivery service that is a part of its pharmacy workflow process that is managed within the pharmacy workflow system in which case the update by the pharmacist would automatically pass the workflow to the pharmacy delivery service to perform the delivery portion of the process. If the hospital has a special delivery service that the pharmacist usually calls after filling a prescription, the Surveillance Gadget system would provide an improved interface 125 which can automatically communicate the alert and action to the delivery workflow system to save time and improve efficiencies.

Also, since the Surveillance Gadget can extract and evaluate information from multiple workflow systems 130, it can also compare the information from different systems to confirm that the handoff of tasks between workflow units is identified and documented properly. For example, when the prescription had been ordered by the physician and was either entered into the nursing workflow system or had been placed with the pharmacist and entered into the pharmacy workflow system, the Surveillance Gadget system could actually set a timely response condition on each step of the process or back-time from the deadline by which the prescription medication should be administered to calculate an anticipated time by which the delivery services would be required. In either event, the mini-screen dashboards of the on-duty pharmacist and the delivery staff can be updated to show the alert for the time-critical medication 140.

By interfacing with different workflow systems, the close of one action in one workflow system that leads to the opening of another action in another workflow system allows Surveillance Gadget system to track and predict the times for the handoffs between workflow units. This information may be evaluated further to improve the speed and efficiency of the handoffs and may allow for closed-loop handoffs. For example, with the closing of a prescription order by the clinical pharmacist by filling the prescription and giving it to delivery, the Surveillance Gadget system may be able to predict that the nursing workflow system should anticipate a delivery of the medication by a particular time so an alert may be sent to the responsible nurse's mini-screen dashboard to check on the status of the medication if the prescription is not filled by a particular time in the overall workflow process (or if the Surveillance Gadget system has not been updated by this time to show that the prescription had been filled). Additionally, the responsible nurse's mini-screen can include the alert that the medication should be administered before the deadline, and the mini-screen of the delivery staff can be notified in advance that a member of the delivery staff should be prepared to pick up the medication and deliver it to the nursing station by a particular time. In the closed-loop system, the clinical pharmacist's closed action would be confirmed when the nursing workflow system indicates that the prescription has been administered.

When the delivery of the time-critical medication is made to the nursing station, the delivery services staff has a nurse sign off on its receipt so that the delivery workflow system closes the open item. In this case, it is assumed that there is no linkage between the delivery workflow system and the nursing workflow system so the Surveillance Gadget system provides the interface that links the end of the prescription filling and delivery workflow processes with the beginning of the medication administration workflow process in the nursing workflow system. Accordingly, the delivery workflow system communicates the change in status to the Surveillance Gadget system which then automatically removes the delivery item from the mini-screen dashboard of the delivery staff. In the closed-loop system, the Surveillance Gadget system could provide an alert if the nurse who had received the medication does not enter the receipt or administration of the medication into the nursing workflow system within a certain period of time after the delivery staff having updated the delivery workflow system. When the nurse administers the medication to the patient and updates the nursing workflow system, the updated information is communicated to the Surveillance Gadget system which removes the alert and the item from the responsible nurse's mini-screen dashboard.

As another example, consider the situation described above when a patient comes out of surgery and is in recovery waiting for an overnight room. With current healthcare task management systems, there may be a number of different systems that are updated during the transfer of the patient, and while there may be existing interfaces between some of the systems, there may not be an interface through all of the systems or there may not be an efficient way to provide timely information to each one of the people in the sequential chain of care so that work can be optimized across the various systems so that the patient is handed off in a timely manner and without unnecessary waiting times between each step of the transfer process. In the case where the asset management system (AMS) is used to coordinate the transfer of the patient from surgery through recovery and to an overnight room, there may not be any interface between the AMS and the pharmacy information system (PIS) which would permit the identification of patients who should receive a prescription for antibiotics following surgery. With the present invention, the SG system may receive information from both the AMS and PIS and a patient moving from surgery into recovery could cause the AMS to trigger the SG system associated with the patient's attending healthcare provider to enter the appropriate prescription into the orders for the patient which is linked to the PIS, and the SG system associated with the clinical pharmacist would be updated to indicate that there is a new prescription. Therefore, the clinical pharmacist's SG system can have an indicator box for the number of patients requiring antibiotics after surgery but does not need to have an indicator box for the actual number of patients who remain in recovery following surgery because the clinical pharmacist may be able to fill the prescription before the patient is out of recovery which would remove the patient from the pharmacist's post-surgery prescription indicator box while the patient would remain on the indicator box for the patient's recovery healthcare team. Of course, the converse may also be true, such as in the situation where the patient gets out of recovery before the pharmacist fills the prescription. Accordingly, the relevant information may be entered once in the particular system that is used for the management of the particular team's workflow and this information can then be tracked relative to other ancillary systems that support discrete work during certain stages of the workflow or begin a new team's workflow where the other team's workflow ended.

The Surveillance Gadget system is also very good at identifying specific patients out of a large population that require clinical intervention. As healthcare adds more regulatory requirements and quality measure reporting, healthcare professionals more often find themselves analyzing large volumes of data looking for patients who meet specific criteria. Core Measures specialists may use the SG system to search for patients who have just been admitted and have not received needed immunizations or who meet criteria to receive particular treatments.

The combination and fusion of database technologies with workflow systems and an entirely new use of mini-screen dashboards result in a unique and innovative evolution that significantly improves the way that time sensitive information is communicated to healthcare personnel and provides results that would not have been expected in considering the prior uses of these technologies alone, particularly in making time sensitive patient information more easily available to different users of the SG system who are part of a larger overall workflow process but who had previously been isolated from each other due to their use of different workflow systems. The increase in speed and efficiency for communicating the information will change the way healthcare professionals practice medicine and the way healthcare administrators monitor the processes with which care is delivered.

A system user does not need to be logged into a particular clinical software system or one of the workflow systems in order for the mini-screen dashboard to appear. The user can log into the user's account 150 in the SG system, or just the mini-screen dashboard application portion of the SG system, and the SG system maintains the necessary connections to the other systems for communicating and aggregating the information that is necessary for the particular system user's role within the organization. The SG system can be limited to provide the information that a user needs for their particular role 160 and will not provide additional information from all of the other systems so that the user is not overwhelmed by information overload. In order for the system user to launch and use one of the workflow applications or any other application that has password protected accounts, the user must log into such applications.

The SG system is configured to periodically query all of the other systems to update its information and to deliver the updated information to the system users 100. The default update period can be set at one minute although certain systems may be able to use a longer update period, refreshing the SG system database less frequently than the default, while other systems may use a shorter update period, refreshing the SG system database more frequently than the default. The communication of the updated information to the system users is similarly configured with a default reporting period that can be extended or shortened.

The SG system can configure the mini-screen dashboard based on a computer's particular use within the overall system. The computer's use is primarily dependent on the role and duties of the system user who is logged into the SG system. The system preferably uses a standard protocol, such as Clinical Context Object Workgroup (CCOW), which enables disparate applications to synchronize in real time, and at the user-interface level. The protocol is vendor independent and allows applications to present information at the desktop and/or portal level in a unified way. Accordingly, the SG system is able to communicate and aggregate data from the different systems and is able to direct information to particular users based on the roles that they have been given within the system.

As indicated above, some elements in the mini-screen dashboard can provide more detailed information, such as specific lab values (e.g., partial thromboplastin time, PTT), critical lab values that are predefined in the system, new pharmacy orders, point-of-care (POC) glucose readings. For POC glucose readings, the mini-screen dashboard could display the readings with the listing of the respective patients and the system may also display the corresponding sliding scale insulin order that the system calculates so that the mini-screen dashboard includes the instruction on how much insulin the nurse should give to the patient. Such details regarding the order may be provided through the mini-screen dashboard although this is the type of information that would usually be obtained by selecting the particular patient information to launch the appropriate application. Some information in the system could be based on whether there is an appropriate order or could be based on workflow charting; an example would be whether venous thromboembolism (VTE) prophylaxis is completed.

The primary use of the Surveillance Gadget system with a mini-screen dashboard is for workflow purposes (patient's needing medication reconciliation, etc.), core measures (identifying patients who may need something addressed from a core measures perspective), readmission rate (identifying patients at high risk for readmission so some intervention can be performed), etc. Other uses can also be made of the inventive system. For example, by aggregating the information from multiple sources, such as multiple workflow systems, the SG system can automatically prepare reports that previous systems would have had to first correlate. The SG system can format the data in reports that correspond with workflow and healthcare management systems which may perform further processing, computations and evaluations of the data. The data can be formatted so that workflow efficiency can be evaluated and improved. Since the SG system can interface with other systems, it can obtain information from flow sheets, such as Foley catheters, central lines, restraints and other elements that may be documented in electronic health care systems.

According to the exemplary embodiments described herein, the SG system is a form of a targeted surveillance system that uses a unique software application as particularly described with reference to use in the healthcare industry. It is used by caregivers and other healthcare clinicians, quality management personnel and hospital administrators to monitor their patients and the workflow processes required to treat them in accordance with best practice and state and federal regulations. The inventive system can be used by caregivers generally, such as doctors, nurses, physician assistants, and nursing assistants, or other clinicians and medical service providers, including support staff members that do not typically have direct interaction with the patients, such as the pharmacists and lab technicians as well as the staff managers.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For example, although Surveillance Gadget system has its primary applicability directed to uses in the healthcare industry, it will be appreciated that this system may be applied to dashboard systems in any other industry, particularly the industries discussed in the Background section above. Thus, the breadth and scope of the present invention should not be limited by any of the above-described exemplary embodiments, but should be defined only in accordance with the following claims appended hereto and their equivalents.

What is claimed is:

1. A method for providing information on a plurality of healthcare workflow processes, comprising the steps of:
    defining a plurality of patient status criteria corresponding with a plurality of data fields in a centralized database;
    correlating in said centralized database said data fields with a set of indicator boxes;
    updating status information in said centralized database for a plurality of patients;
    identifying in a computer processor sets of patients having status information corresponding with each of said patient status criteria;
    calculating in said computer processor a number of patients in each of said identified sets of patients;
    displaying said number of patients in a series of said indicator boxes on a foreground mini-screen dashboard; and
    repeating said updating, identifying, calculating and displaying steps on a periodic basis;
    wherein said displaying step is further comprised of displaying said foreground mini-screen dashboard over all other displays on a full monitor screen in a semi-transparent view when said mini-screen dashboard is not selected, displaying said foreground mini-screen dashboard in an opaque view when a cursor hovers over said foreground mini-screen dashboard, and displaying names of patients corresponding with said number of patients when one of said indicator boxes is selected.

2. The method of claim 1, further comprising the steps of:
    storing sets of patient information in a healthcare workflow system, wherein said healthcare workflow system is comprised of a plurality of workflow databases containing said patient information, at least one central computer server in communication with said workflow databases, and a plurality of workflow computers in networked communication with said centralized database and having access to said patient information, and wherein said patient information is comprised of said status information and personally identifiable information;
    aggregating said status information from said patient information in said centralized database;
    creating a plurality of user accounts for a plurality of clinicians working with said patients in the healthcare workflow processes, wherein said user accounts have corresponding user access to said centralized database through at least one of said workflow computers;
    correlating in said centralized database a subset of said indicator boxes for each of said user accounts; and
    distributing said number of patients to said corresponding subset of said indicator boxes for each of said user accounts having said mini-screen dashboard at said workflow computers.

3. The method of claim 2, further comprising the step of defining an interface between the healthcare workflow processes as an end of a first healthcare workflow process for a first clinician and a beginning of a second healthcare workflow process for a second clinician.

4. The method of claim 3, wherein said first healthcare workflow process is a surgical procedure and said second healthcare workflow process is an administration of an antibiotic prescription, and wherein said workflow computers are selected from the group of computers consisting of a desktop computer, a laptop computer, a tablet computer, a smart-phone, and any combination thereof.

5. The method of claim 1, further comprising the step of providing a selectable configuration for said indicator boxes displayed on said foreground mini-screen dashboard, wherein a first selected configuration is comprised of a first subset of indicator boxes and a second selected configuration is comprised of a second subset of indicator boxes.

6. The method of claim 5, wherein said patient status criteria for said selectable configuration is selected from a group of status criteria consisting of a clinical intervention status, a prescription medication status, a time-critical action status, and a workflow interface status, and any combination thereof.

7. The method of claim 1, wherein said displaying step is further comprised of displaying a heading name of said patient status criteria when said cursor hovers over one of said indicator boxes.

8. The method of claim 7, wherein said foreground mini-screen dashboard has an area less than approximately one twentieth a size of said full monitor screen.

9. The method of claim 7, wherein said displaying step is further comprised of displaying an alert for at least one of a time-critical action and a workflow interface status change.

10. The method of claim 1, further comprising the steps of assigning a workflow application to at least one of said indicator boxes and activating said workflow application when said corresponding one of said indicator boxes is selected.

11. A system for providing information on a plurality of healthcare workflow processes, comprising:
a centralized database comprising a plurality of patient status criteria corresponding with a plurality of data fields and status information for a plurality of patients;
a computer processor in communication with said centralized database, wherein said computer processor identifies sets of patients having status information corresponding with each of said patient status criteria and calculates a number of patients in each of said identified sets of patients;
a plurality of workflow computers in networked communication with said centralized database, wherein said workflow computers comprise sets of indicator boxes correlated with said data fields and a monitor screen having a full display and a foreground mini-screen dashboard, wherein said number of patients are displayed in a series of said indicator boxes on said foreground mini-screen dashboard, and wherein said number of patients displayed in said series of said indicator boxes is periodically refreshed with updates to said patient status criteria from said centralized database, wherein said workflow computers display said foreground mini-screen dashboard over all other displays on said monitor screen in a semi-transparent view when said mini-screen dashboard is not selected, wherein said workflow computers display said foreground mini-screen dashboard in an opaque view when a cursor hovers over said foreground mini-screen dashboard, and wherein said workflow computers display names of patients corresponding with said number of patients when one of said indicator boxes is selected.

12. The system of claim 11, wherein said foreground mini-screen dashboard is comprised of a selectable configuration for said indicator boxes, wherein a first selected configuration is comprised of a first subset of indicator boxes and a second selected configuration is comprised of a second subset of indicator boxes.

13. The system of claim 11, wherein said workflow computers display an alert for at least one of a time-critical action and a workflow interface status changes.

14. The system of claim 11, wherein a workflow application is correlated to a selection of at least one of said indicator boxes, and wherein said workflow computers activate said workflow application according to said selection.

\* \* \* \* \*